(12) United States Patent
Velikyan et al.

(10) Patent No.: US 8,007,766 B2
(45) Date of Patent: Aug. 30, 2011

(54) MICROWAVE METHOD FOR PREPARING RADIOLABELLED GALLIUM COMPLEXES

(75) Inventors: Irina Velikyan, Uppsala (SE); Bengt Langstrom, Uppsala (SE)

(73) Assignee: GE Healthcare Limited, Little Chalfont (GB)

( * ) Notice: Subject to any disclaimer, the term of this patent is extended or adjusted under 35 U.S.C. 154(b) by 0 days.

(21) Appl. No.: 10/552,134

(22) PCT Filed: Apr. 8, 2004

(86) PCT No.: PCT/GB2004/001550
§ 371 (c)(1),
(2), (4) Date: Sep. 14, 2006

(87) PCT Pub. No.: WO2004/089425
PCT Pub. Date: Oct. 21, 2004

(65) Prior Publication Data
US 2007/0027307 A1    Feb. 1, 2007

(30) Foreign Application Priority Data
Apr. 11, 2003   (GB) .................................. 0308408.4

(51) Int. Cl.
A61K 51/00    (2006.01)
A61M 36/14    (2006.01)

(52) U.S. Cl. ..................................... 424/1.11; 424/1.65

(58) Field of Classification Search .................. 424/1.65
See application file for complete search history.

(56) References Cited

U.S. PATENT DOCUMENTS

| 5,029,065 | A |   | 7/1991 | Nau et al. |   |
|---|---|---|---|---|---|
| 5,439,863 | A | * | 8/1995 | Bottcher et al. | 502/152 |
| 5,607,659 | A | * | 3/1997 | Gustavson et al. | 424/1.73 |

FOREIGN PATENT DOCUMENTS

| GB | 2056471 A | * | 3/1981 |
|---|---|---|---|
| WO | 95/33757 |   | 12/1995 |
| WO | 99/56791 |   | 11/1999 |
| WO | WO 03059397 A2 | * | 7/2003 |

OTHER PUBLICATIONS

Yngve (Int. Diss. Abs. 2001, 62, abstract).*
Lidström et al. (Tetrahedron 2001, 57, 9225-9283).*
Wheaton et al. (Industrial and Engineering Chemistry 1951, 43, 1088-1093).*
Morrissey, et.al.: "Microwave Preparation of Technetium-99m-sulfur Colloid" Journal of Nuclear Medicine Technology, Society of Nuclear Medicine, New York, NJ vol. 20, No. 3, Sep. 1992 pp. 159-162.
McCarthy T.J. et.al.: "Application of Microwave Heating to the Synthesis of U18FFLUOROMISONIDAZOLE" Applied Radiation and Isotopes, Pergamon Press Ltd., Exeter, GB vol. 44, No. 8, Aug. 1993, pp. 1129-1132.
Stone-Elander S., et.al.: "Fast Chemistry in Microwave Fields: Nucleophilic <18>F-Radiofluorinations of Aromatic Molecules" Applied Radiation and Isotopes 1993 United Kingdom, vol. 44 No. 5, 1993, pp. 889-893.
Ugur, O., et.al.,Nuclear Med. Biology, vol. 29, 2002, Ga-66 Labeled Somatostatin Analogue DOTA-DPhe1-Tyr3-Octreotide as a Potential Agent for Positron Emission Tomography Imaging and Receptor Mediated Internal Radiotherapy of Somatostatin Receptor Positive Tumors, pp. 147-157.
Stone-Elanders, S. et.al., J. Labelled Comp. Radiopharm. Vo. 45, 2002 Microwave applications in radiolabelling with short-lived positron-emitting radionuclides, pp. 715-746.
Elander, N., et.al., Chem. Soc.Rev., vol. 29, 2000 Microwave-enhanced labeling procedures, pp. 239-249, pp. 239 and 240 missing.
Int'l search report/written opinion PCT/GB2004/001550 Dated Aug. 2004.
GB Search report 0308408.4 dated Sep. 2003.

* cited by examiner

Primary Examiner — Michael G Hartley
Assistant Examiner — Melissa Perreira
(74) Attorney, Agent, or Firm — Yonggang Ji

(57) ABSTRACT

The present invention relates to a method of producing radiolabelled gallium complexes that could be used as diagnostic agents, e.g. for positron emission tomography (PET) imaging.

13 Claims, No Drawings

MICROWAVE METHOD FOR PREPARING RADIOLABELLED GALLIUM COMPLEXES

This application is a filing under 35 U.S.C. 371 of international application number PCT/GB2004/001550, filed Apr. 8, 2004, which claims priority to application number 0308408.4 filed Apr. 11, 2003, in Great Britain the entire disclosure of which is hereby incorporated by reference.

The present invention relates to a method of producing radiolabelled gallium complexes. The complexes could be used as diagnostic agents, e.g. for positron emission tomography (PET) imaging.

PET imaging is a tomographic nuclear imaging technique that uses radioactive tracer molecules that emit positrons. When a positron meets an electron, the both are annihilated and the result is a release of energy in form of gamma rays, which are detected by the PET scanner. By employing natural substances that are used by the body as tracer molecules, PET does not only provide information about structures in the body but also information about the physiological function of the body or certain areas therein. A common tracer molecule is for instance 2-fluoro-2-deoxy-D-glucose (FDG), which is similar to naturally occurring glucose, with the addition of a $^{18}$F-atom. Gamma radiation produced from said positron-emitting fluorine is detected by the PET scanner and shows the metabolism of FDG in certain areas or tissues of the body, e.g. in the brain or the heart. The choice of tracer molecule depends on what is being scanned. Generally, a tracer is chosen that will accumulate in the area of interest, or be selectively taken up by a certain type of tissue, e.g. cancer cells. Scanning consists of either a dynamic series or a static image obtained after an interval during which the radioactive tracer molecule enters the biochemical process of interest. The scanner detects the spatial and temporal distribution of the tracer molecule. PET also is a quantitative imaging method allowing the measurement of regional concentrations of the radioactive tracer molecule.

Commonly used radionuclides in PET tracers are $^{11}$C, $^{18}$F, $^{15}$O $^{13}$N or $^{76}$Br. Recently, new PET tracers were produced that are based on radiolabelled metal complexes comprising a bifunctional chelating agent and a radiometal Bifunctional chelating agents are chelating agents that coordinate to a metal ion and are linked to a targeting vector that will bind to a target site in the patient's body. Such a targeting vector may be a peptide that binds to a certain receptor, probably associated with a certain area in the body or with a certain disease. A targeting vector may also be an oligonucleotide specific for e.g. an activated oncogene and thus aimed for tumour localisation. The advantage of such complexes is that the bifunctional chelating agents may be labelled with a variety of radiometals like, for instance, $^{68}$Ga, $^{213}$Bi or $^{86}$Y. In this way, radiolabelled complexes with special properties may be "tailored" for certain applications.

$^{68}$Ga is of special interest for the production of Ga-radiolabelled metal complexes used as tracer molecules in PET imaging. $^{68}$Ga is obtained from a $^{68}$Ge/$^{68}$Ga generator, which means that no cyclotron is required. $^{68}$Ga decays to 89% by positron emission of 2.92 MeV and its 68 min half life is sufficient to follow many biochemical processes in vivo without unnecessary radiation. With its oxidation state of +III, $^{68}$Ga forms stable complexes with various types of chelating agents and $^{68}$Ga tracers have been used for brain, renal, bone, blood pool, lung and tumour imaging.

J. Schumacher et al., Cancer Res. 61, 2001, 3712-3717 describe the synthesis of $^{68}$Ga—N,N'[2-hydroxy-5-(ethylene-β-carboxy)benzyl]ethylenediamine-N,N'-diacetic acid ($^{68}$Ga-HBED-CC). $^{68}$Ga obtained from a $^{68}$Ge/$^{68}$Ga generator and Ga$^{3+}$ carrier are reacted with the chelating agent HBED-CC in acetate buffer for 15 min at 95° C. Uncomplexed $^{68}$Ga is separated from the complex using a cation exchange column. The overall preparation is reported to take 70 min. A disadvantage of this method is that the overall preparation time of the radiolabelled complex is very long. Due to the addition of "cold" Ga$^{3+}$ carrier, the specific activity of the reaction is low. Moreover, the radiolabelled complex had to be purified after the complex formation reaction.

WO-A-99/56791 discloses the reaction of $^{68}$GaCl$_3$ obtained from a $^{68}$Ge/$^{68}$Ga generator with the tetradentate amine trithiolate chelating agent tris(2-mercaptobenzyl)amine (S$_3$N). The complex formation is carried out at room temperature for 10 min. A disadvantage of the method described is that the radiolabelled complex had to be purified by liquid chromatography before it could be used for in vivo studies. A further disadvantage of the method is the relatively long reaction time.

Ö. Ugur et al., Nucl. Med. Biol. 29, 2002, 147-157 describe the synthesis of the $^{68}$Ga labelled somatostatin analogue DOTA-DPhe$^1$-Tyr$^3$-octreotide (DOTATOC). The compound is prepared by reacting $^{68}$GaCl$_3$ obtained from a $^{68}$Ge/$^{68}$Ga generator with the chelating agent DOTATOC for 15 min at 100° C. A disadvantage of this method is that the reaction mixture had to be heated at relatively high temperatures. The DOTA chelating agent was functionalised with a peptide targeting vector and peptides and proteins are substances, which are known to be sensitive to heat. Thus, with the method described there is a risk that heat sensitive targeting vectors are destroyed during complex formation. A further disadvantage is that the complex had to be purified by HPLC before it could be used for animal studies.

U.S. Pat. No. 5,070,346 discloses $^{68}$Ga-labelled complexes of the chelating agent tetraethylcyclohexyl-bis-aminoethanethiol (BAT-TECH). The complexes are synthesised by reacting $^{68}$GaCl$_3$ obtained from a $^{68}$Ge/$^{68}$Ga generator with BAT-TECH at 75° C. for 15 min and subsequent filtration. The preparation of the complex was accomplished in 40 min. Due to the high reaction temperature; this method would not be suitable for bifunctional chelating agents comprising a heat sensitive targeting vector, for instance a peptide or a protein. A further disadvantage is the long reaction time of the complex formation reaction.

In view of the relatively short half-life of $^{68}$Ga there is a need for a fast method for the synthesis of $^{68}$Ga-labelled complexes, which could be used as tracer molecules for PET imaging.

It has now been found that the use of microwave activation substantially improves the efficiency and reproducibility of the $^{68}$Ga-chelating agent complex formation. Due to microwave activation, chemical reaction times could be shortened substantially; i.e. the reaction is completed within 2 min and less. This is a clear improvement as a 10 minutes shortage of the reaction time saves about 10% of the $^{68}$Ga activity. Furthermore, microwave activation also leads to fewer side reactions and to an increased radiochemical yield, which is due to increased selectivity. Solutions of $^{66}$Ga$^{3+}$, $^{67}$Ga$^{3+}$ and $^{68}$Ga$^{3+}$ radioisotopes, which have been obtained by cyclotron production or from a generator contain so-called pseudo carriers, i.e. other metal cations like for instance Fe$^{3+}$, Al$^{3+}$, Cu$^{2+}$, Zn$^{2+}$ and In$^{3+}$. As these pseudo carriers compete with Ga$^{3+}$ in the complex formation reaction, it is important to increase the selectivity of the radiolabelling reaction. Hence, microwave activation has a positive effect on radiolabelling with all Ga-radioisotopes, namely with $^{66}$Ga, $^{67}$Ga and $^{68}$Ga.

Microwave activation has been used in nucleophilic aromatic radiofluorations with $^{18}$F and it was found that comparable or better yields than those reported for thermal treatments were obtained in shorter reaction times (S. Stone-Elander et al., Appl. Rad. Isotopes 44(5), 1993, 889-893). However, the use of microwave activation in Ga-radiolabelling reactions has not been described yet.

The invention thus provides a method of producing a radiolabelled gallium complex by reacting a $Ga^{3+}$ radioisotope with a chelating agent characterised in that the reaction is carried out using microwave activation.

Suitable $Ga^{3+}$ radioisotopes according to the invention are $^{66}Ga^{3+}$, $^{67}Ga^{3+}$ and $^{68}Ga^{3+}$, preferably $^{66}Ga^{3+}$ and $^{68}Ga^{3+}$ and particularly preferably $^{68}Ga^{3+}$. $^{66}Ga^{3+}$ and $^{68}Ga^{3+}$ are particularly suitable for the production of radiolabelled complexes useful in PET imaging whereas $^{67}Ga^{3+}$ is particularly suitable for the production of radiolabelled complexes useful in single photon emission computerised tomography (SPECT).

$^{66}Ga^{3+}$ is obtainable by cyclotron production by irradiation of elemental zinc targets. To minimise the amounts of $^{67}Ga$ production, the target thickness is preferably maintained such that the degraded proton energy is above 8 MeV, and irradiation time is kept short, e.g. <4 hrs. The chemical separation may be achieved using solvent-solvent extraction techniques using isopropyl ether and HCl as described in L. C. Brown, Int. J. Appl. Radiat. Isot. 22, 1971, 710-713. $^{66}Ga$ has a relatively long half-life of 9.5 h and the most abundant positron emitted has a uniquely high energy of 4.2 MeV.

$^{67}Ga^{3+}$ is obtainable by cyclotron production and $^{67}GaCl_3$ obtained by cyclotron production is a commercially available compound. The half-life of $^{67}Ga$ is 78 h.

$^{68}Ga$ is obtainable from a $^{68}Ge/^{68}Ga$ generator. Such generators are known in the art and for instance described by C. Loc'h et al, J. Nucl. Med. 21, 1980, 171-173. Generally, $^{68}Ge$ is loaded onto a column consisting of an organic resin or an inorganic metal oxide like tin dioxide, aluminium dioxide or titanium dioxide. $^{68}Ga$ is eluted from the column with aqueous HCl, yielding $^{68}GaCl_3$. $^{68}Ga^{3+}$ is particularly preferred in the method according to the invention as its production does not require a cyclotron and its 68 min half-life is sufficient to follow many biochemical processes in vivo by PET imaging without long radiation.

Preferred chelating agents for use in the method of the invention are those which present the $Ga^{3+}$ radioisotopes in a physiologically tolerable form. Further preferred chelating agents are those that form complexes with $Ga^{3+}$ radioisotopes that are stable for the time needed for diagnostic investigations using the radiolabelled complexes.

Suitable chelating agents are, for instance, polyaminopolyacid chelating agents like DTPA, EDTA, DTPA-BMA, DOA3, DOTA, HP-DOA3, TMT or DPDP. Those chelating agents are well known for radiopharmaceuticals and radiodiagnosticals. Their use and synthesis are described in, for example, U.S. Pat. No. 4,647,447, U.S. Pat. No. 5,362,475, U.S. Pat. No. 5,534,241, U.S. Pat. No. 5,358,704, U.S. Pat. No. 5,198,208, U.S. Pat. No. 4,963,344, EP-A-230893, EP-A-130934, EP-A-606683, EP-A-438206, EP-A-434345, WO-A-97/00087, WO-A-96/40274, WO-A-96/30377, WO-A-96/28420, WO-A-96/16678, WO-A-96/11023, WO-A-95/32741, WO-A-95/27705, WO-A-95/26754, WO-A-95/28967, WO-A-95/28392, WO-A-95/24225, WO-A-95/17920, WO-A-95/15319, WO-A-95/09848, WO-A-94/27644, WO-A-94/22368, WO-A-94/08624, WO-A-93/16375, WO-A-93/06868, WO-A-92/11232, WO-A-92/09884, WO-A-92/08707, WO-A-91/15467, WO-A-91/10669, WO-A-91/10645, WO-A-91/07191, WO-A-91/05762, WO-A-90/12050, WO-A-90/03804, WO-A-89/00052, WO-A-89/00557, WO-A-88/01178, WO-A-86/02841 and WO-A-86/02005.

Suitable chelating agents include macrocyclic chelating agents e.g. porphyrin-like molecules and pentaaza-macrocycles as described by Zhang et al., Inorg. Chem. 37(5), 1998, 956-963, phthalocyanines, crown ethers, e.g. nitrogen crown ethers such as the sepulchrates, cryptates etc., hemin (protoporphyrin IX chloride), heme and chelating agents having a square-planar symmetry.

Macrocyclic chelating agents are preferably used in the method of the invention. In a preferred embodiment, these macrocyclic chelating agents comprise at least one hard donor atom such as oxygen and/or nitrogen like in polyaza- and polyoxomacrocycles. Preferred examples of polyazamacrocyclic chelating agents include DOTA, TRITA, TETA and HETA with DOTA being particularly preferred.

Particularly preferred macrocyclic chelating agents comprise functional groups such as carboxyl groups or amine groups which are not essential for coordinating to $Ga^{3+}$ and thus may be used to couple other molecules, e.g. targeting vectors, to the chelating agent. Examples of such macrocyclic chelating agents comprising functional groups are DOTA, TRITA or HETA.

In a further preferred embodiment, bifunctional chelating agents are used in the method according to the invention. "Bifunctional chelating agent" in the context of the invention means chelating agents that are linked to a targeting vector. Suitable targeting vectors for bifunctional chelating agents useful in the method according to the invention are chemical or biological moieties, which bind to target sites in a patient's body, when the radiolabelled gallium complexes comprising said targeting vectors have been administered to the patient's body. Suitable targeting vectors for bifunctional chelating agents useful in the method according to the invention are proteins, glycoproteins, lipoproteins, polypeptides like antibodies or antibody fragments, glycopolypeptides, lipopolypeptides, peptides, like RGD binding peptides, glycopeptides, lipopeptides, carbohydrates, nucleic acids e.g. DNA, RNA, oligonucleotides like antisense oligonucleotides or a part, a fragment, a derivative or a complex of the aforesaid compounds, or any other chemical compound of interest like relatively small organic molecules, particularly small organic molecules of less than 2000 Da.

In a particularly preferred embodiment, macrocyclic bifunctional chelating agents are used in the method according to the invention. Preferred macrocyclic bifunctional chelating agents comprise DOTA, TRITA or HETA linked to a targeting vector, preferably to a targeting vector selected from the group consisting of proteins, glycoproteins, lipoproteins, polypeptides, glycopolypeptides, lipopolypeptides, peptides, glycopeptides, lipopeptides carbohydrates, nucleic acids, oligonucleotides or a part, a fragment, a derivative or a complex of the aforesaid compounds and small organic molecules; particularly preferably to a targeting vector selected from the group consisting of peptides and oligonucleotides.

The targeting vector can be linked to the chelating agent via a linker group or via a spacer molecule. Examples of linker groups are disulfides, ester or amides, examples of spacer molecules are chain-like molecules, e.g. lysin or hexylamine or short peptide-based spacers. In a preferred embodiment, the linkage between the targeting vector and the chelating agent part of radiolabelled gallium complex is as such that the targeting vector can interact with its target in the body without being blocked or hindered by the presence of the radiolabelled gallium complex.

Microwave activation according to the invention is suitably carried out by using a microwave oven, preferably by using a monomodal microwave oven as. Suitably microwave activation is carried out at 80 to 120 W, preferably at 90 to 110 W, particularly preferably at about 100 W. Suitable microwave activation times range from 20 s to 2 min, preferably from 30 s to 90 s, particularly preferably from 45 s to 60 s.

A temperature control of the reaction is advisable when temperature sensitive chelating agents, like for instance bifunctional chelating agents comprising peptides or proteins as targeting vectors, are employed in the method according to the invention. Duration of the microwave activation should be adjusted in such a way, that the temperature of the reaction mixture does not lead to the decomposition of the chelating agent and/or the targeting vector. If chelating agents used in the method according to the invention comprise peptides or proteins, higher temperatures applied for a shorter time are generally more favourable than lower temperatures applied for a longer time period.

Microwave activation can be carried out continuously or in several microwave activation cycles during the course of the reaction.

In a preferred embodiment, the invention provides a method of producing a $^{68}$Ga radiolabelled PET imaging tracer by reacting $^{68}$Ga$^{3+}$ with a macrocyclic bifunctional chelating agent comprising hard donor atoms, characterised in that the reaction is carried out using microwave activation.

In a particularly preferred embodiment of the method described in the last preceding paragraph, the microwave activation is carried out from 30 s to 90 s at 90 to 110 W.

If $^{68}$Ga$^{3+}$ is used in the method according to the invention, the $^{68}$Ga$^{3+}$ is preferably obtained by contacting the eluate form a $^{68}$Ge/$^{68}$Ga generator with an anion exchanger and eluting $^{68}$Ga$^{3+}$ from said anion exchanger. In a preferred embodiment, the anion exchanger is an anion exchanger comprising HCO$_3^-$ as counterions.

The use of anion exchangers to treat $^{68}$Ga eluate obtained from a $^{68}$Ge/$^{68}$Ga generator is described by J. Schuhmacher et al. Int. J. appl. Radiat. Isotopes 32, 1981, 31-36. A Bio-Rad AG 1×8 anion exchanger was used for treating the 4.5 N H Cl $^{68}$Ga eluate obtained from a $^{68}$Ge/$^{68}$Ga generator in order to decrease the amount of $^{68}$Ge present in the eluate.

It has now been found that the use of anion exchangers comprising HCO$_3^-$ as counterions is particularly suitable for the purification and concentration of the generator eluate. Not only the amount of $^{68}$Ge present in the eluate could be reduced but also the amount of so-called pseudo carriers, i.e. other metal cations like Fe$^{3+}$, Al$^{3+}$, Cu$^{2+}$, Zn$^{2+}$ and In$^{3+}$, that are eluted together with the $^{68}$Ga$^{3+}$ from the generator. As these pseudo carriers compete with $^{68}$Ga$^{3+}$ in the subsequent complex formation reaction, it is especially favourable to reduce the amount of those cations as much as possible before the labelling reaction. A further advantage of the anion-exchange purification step is that the concentration of $^{68}$Ga$^{3+}$, which is in the picomolar to nanomolar range after the elution, can be increased up to a nanomolar to micromolar level. Hence, it is possible to reduce the amount of chelating agent in a subsequent complex formation reaction, which considerably increases the specific radioactivity. This result is important for the production of $^{68}$Ga-radiolabelled PET tracers that comprise a bifunctional chelating agent; i.e. a chelating agent linked to a targeting vector, as the increase in specific radioactivity enables the reduction in amount of such tracers when used in a patient.

Hence, another preferred embodiment of the method according to the invention is a method of producing a $^{68}$Ga-radiolabelled complex by reacting $^{68}$Ga$^{3+}$ with a chelating agent using microwave activation, wherein the $^{68}$Ga$^{3+}$ is obtained by contacting the eluate form a $^{68}$Ge/$^{68}$Ga generator with an anion exchanger, preferably with an anion exchanger comprising HCO$_3^-$ as counterions, and eluting $^{68}$Ga$^{3+}$ from said anion exchanger.

$^{68}$Ge/$^{68}$Ga generators are known in the art, see for instance C. Loc'h et al, J. Nucl. Med. 21, 1980, 171-173 or J. Schuhmacher et al. Int. J. appl. Radiat. Isotopes 32, 1981, 31-36. $^{68}$Ge may be obtained by cyclotron production by irradiation of, for instance Ga$_2$(SO$_4$)$_3$ with 20 MeV protons. It is also commercially available, e.g. as $^{68}$Ge in 0.5 M HCl. Generally, $^{68}$Ge is loaded onto a column consisting of organic resin or an inorganic metal oxide like tin dioxide, aluminium dioxide or titanium dioxide. $^{68}$Ga is eluted from the column with aqueous HCl yielding $^{68}$GaCl$_3$.

Suitable columns for $^{68}$Ge/$^{68}$Ga generators consist of inorganic oxides like aluminium dioxide, titanium dioxide or tin dioxide or organic resins like resins comprising phenolic hydroxyl groups (U.S. Pat. No. 4,264,468) or pyrogallol (J. Schuhmacher et al., Int. J. appl. Radiat. Isotopes 32, 1981, 31-36). In a preferred embodiment, a $^{68}$Ge/$^{68}$Ga generator comprising a column comprising titanium dioxide is used in the method according to the invention.

The concentration of the aqueous HCl used to elute the $^{68}$Ga from the $^{68}$Ge/$^{68}$Ga generator column depends on the column material. Suitably 0.05 to 5 M HCl is used for elution of $^{68}$Ga. In a preferred embodiment, the eluate is obtained from a $^{68}$Ge/$^{68}$Ga generator comprising a column comprising titanium dioxide and $^{68}$Ga is eluted using 0.05 to 0.1 M HCl, preferably about 0.1 M HCl.

In a preferred embodiment of the method according to the invention, a strong anion exchanger comprising HCO$_3^-$ as counterions, preferably a strong anion exchanger comprising HCO$_3^-$ as counterions, is used. In a further preferred embodiment, this anion exchanger comprises quaternary amine functional groups. In another further preferred embodiment, this anion exchanger is a strong anion exchange resin based on polystyrene-divinylbenzene. In a particularly preferred embodiment, the anion exchanger used in the method according to the invention is a strong anion exchange resin comprising HCO$_3^-$ as counterions, quaternary amine functional groups and the resin is based on polystyrene-divinylbenzene.

Suitably, water is used to elute the $^{68}$Ga from the anion exchanger in the method according to the invention.

EXAMPLES

Examples 1

Comparison of $^{68}$Ga-radiolabelling of DOTA-D-Phe$^3$-Tyr$^1$-Octreotide (DOTA-TOC) Using Conventional Heating and Microwave Activation 1a) $^{68}$Ga-radiolabelling of DOTA-TOC Using Conventional Heating Sodium acetate was added to the eluate from a $^{68}$Ge/$^{68}$Ga-generator (36 mg to 1 mL) to adjust the pH of the eluate to approximately 5.5 and the mixture was vortexed well. DOTA-TOC (20 nmol) was added and the reaction mixture was heated at 96° C. for 25 min. The reaction mixture was cooled to room temperature and applied to a C-18 SPE-column (HyperSEP S C18), which was then washed with 2 mL H$_2$O and the product was eluted with ethanol: water 50:50 (1 mL).

The reaction mixture and the product were analysed by HPLC using Vydac RP and Fast Desalting HR 10/10 FPLC gel filtration columns.

The analytical radiochemical yield (RCY) was 67%.
The isolated RCY was 34%.

Electrospray ionization mass spectrometry, ESI-MS, was performed on Fisons Platform (Micromass, Manchester, UK), using positive mode scanning and detecting $[M+2H]^{2+}$. DOTATOC was detected at m/z=711.26 and authentic Ga-DOTATOC was detected at m/z=746.0 (calculated m/z=746.5).

1b) $^{68}$Ga-Radiolabelling of DOTA-TOC Using Microwave Activation

The reaction mixture was prepared identically as described under 1a) and transferred into a Pyrex glass vial for microwave activation for 1 min at 100 W. The reaction mixture was cooled to room temperature and applied to a C-18 SPE-column (HyperSEP S C18), which was then washed with 2 mL H$_2$O and the product was eluted with ethanol:water 50:50 (1 mL).

The reaction mixture and the product were analysed by HPLC using Vydac RP and Fast Desalting HR 10/10 FPLC gel filtration columns.

The analytical RCY was over 98%.

The isolated RCY was 70%.

Electrospray ionization mass spectrometry, ESI-MS, was performed on Fisons Platform (Micromass, Manchester, UK), using positive mode scanning and detecting $[M+2H]^{2+}$. DOTATOC was detected at m/z=711.26 and authentic Ga-DOTATOC was detected at m/z=746.0 (calculated m/z=746.5).

1c) Results of the Comparison

In the case of microwave activation, the amount of radioactive material and the product specific activity was increased by 21%. The isolated radiochemical yield was increased 2 fold compared to the results obtained with conventional heating. As the radiochemical yield of the reaction mixture in case of microwave activation was over 98%, a further purification would not have been necessary and the crude reaction mixture could have been used for in vivo application.

Example 2

$^{68}$Ga Radiolabelling of DOTA Linked to Oligonucleotides

In a first step, four different antisense oligonucleotides specific for activated human K-ras oncogene were linked to DOTA:

17-mer phosphodiester oligonucleotide with hexylaminolinker at 5' end;
17-mer phosphodiester oligonucleotide with hexylaminolinker at 3' end;
17-mer phosphorothioate oligonucleotide with hexylaminolinker at 5' end; and
2'-O-methyl phosphodiester with hexylaminolinker at 5' end.

2a) Conjugation of DOTA to Oligonucleotides:

DOTA (32 mg, 66 µmol) and Sulfo-NHS (14 mg, 65 µmol) in H$_2$O (250 µl) were added to EDC (13 mg, 68 µmol) in H$_2$O (250 µl), stirred on ice for 30 min and then warmed to room temperature to give DOTA-sulfo-NHS. A 100 fold excess of DOTA-NHS solution was added dropwise to the oligonucleotide (70-450 nmol) in 1M carbonate buffer (pH 9) and then cooled on ice. The mixture was left at room temperature for 10 hours. The reaction mixture was first purified by gel filtration with NAP 5 columns, eluted with H$_2$O and 100 µL of 1M TEAA (triethylammonium acetate buffer) was added to 1 mL of the product eluate. The product eluate was then applied to a C-18 SPE column (Supelco), the column was washed with 50 mM TEAA (5 mL), 50 mM TEAA containing 5% acetonitrile (3 mL) and the DOTA-oligonucleotide was eluted with water:acetonitrile 50:50 (1 mL). The water-acetonitrile fraction was dried using a vacuum centrifuge. The products were analysed using electrospray ionization mass spectrometry. Analysis in negative mode after direct infusion resulted in the following data: 1. DOTA-phosphodiester: MS (ESI$^-$) m/z: 662.27 $[M-8H]^{8-}$; 756.36 $[M-7H]^{7-}$; 882.91 $[M-6H]^{6-}$. Reconstitution of the data gave M=5303.71; 2. DOTA-phosphorotioate: MS (ES$^-$) m/z: 656.58 $[M-8H]^{9-}$; 738.56 $[M-7H]^{8-}$. Reconstitution of the data gave M=5917.35; 3. DOTA-2'-O-methyl phosphodiester: MS (ESI$^-$) m/z: 674.02 $[M-6H]^{9-}$; 770.19 $[M-8H]^{8-}$; 885.00 $[M-7H]^{7-}$. Reconstitution of the data gave M=6148.84.

2b) $^{68}$Ga-Radiolabelling

Sodium acetate was added to the eluate from a $^{68}$Ge/$^{68}$Ga-generator (36 mg to 1 ml) to adjust the pH of the eluate to approximately 5.5 and the mixture was vortexed well. DOTA-oligonucleotide (10-100 nmol) was added and the mixture was transferred into a Pyrex glass vial for microwave activation for 1 min at 100 W. The reaction mixture was cooled to room temperature then 1 mL of 150 mM TEAA in H$_2$O was added. The mixture was applied to a C-18 SPE-column (Supelco), which was then washed with 50 mM TEAA (1 mL), 50 mM TEAA containing 5% acetonitrile (1 mL). The product was eluted with ethanol: water 50:50 (1 mL) or water:acetonitrile 50:50 (1 mL). The reaction mixture was analysed by HPLC using Vydac RP and Fast Desalting HR 10/10 FPLC gel filtration columns. The analytical RCY ranged from 50% to 70%, the isolated RCY ranged from 30 to 52%. Larger amounts of stronger eluents might improve the isolated RCY.

Example 3

$^{68}$Ga Radiolabelling of DOTA Linked to Peptides

In a first step, four different peptides were linked to DOTA:
Vasoactive Intestinal Peptide (VIP); 28 amino acid residues;
Neuropeptide Y Fragment 18-36 (NPY); 19 amino acid residues;
Pancreastatin Fragment 37-52 (P); 16 amino acid residues; and
Angiotensin II (A); 8 amino acid residues.

3a) Conjugation of DOTA to Peptides:

Conjugation was carried out as described in 2a) using peptides (0.5-3 µmol) instead of oligonucleotides.

The reaction mixtures and products were analysed by HPLC using Vydac RP and Fast Desalting HR 10/10 FPLC gel filtration columns. Electrospray ionization mass spectrometry, ESI-MS, was performed on Fisons Platform (Micromass, Manchester, UK), using positive mode scanning and detecting $[M+2H]^{2+}$, $[M+4H]^{4+}$ and $[M+5H]^{5+}$. VIP was detected at m/z=832.07 $[M+4H]^{4+}$. (DOTA)$_2$-VIP was detected at m/z=1025.00 $[M+4H]^{4+}$. (DOTA)$_3$-VIP was detected at m/z=1122.0 $[M+4H]^{4+}$, (DOTA)$_4$-VIP was detected at m/z=1218.00 $[M+4H]^{4+}$. NPY was detected at m/z=819.31 $[M+3H]^{3+}$. DOTA-NPY was detected at m/z=948.18 $[M+3H]^{3+}$. P was detected at m/z=909.55 $[M+2H]^{2+}$. DOTA-P was detected at m/z=1103.02 $[M+2H]^{2+}$. A was detected at m/z=524.1 $[M+2H]^{2+}$ and DOTA-A was detected at m/z=717.20 $[M+2H]^{2+}$.

3b) $^{68}$Ga-Radiolabelling $^{68}$Ga-radiolabelling was carried out as described in 2b) using 10-20 nmol DOTA-peptide.

The reaction mixture was analysed by HPLC using Vydac RP and Fast Desalting HR 10/10 FPLC gel filtration columns. The analytical RCY ranged from 80% to 90%, the isolated RCY ranged from 60 to 70%. Larger amounts of stronger eluents might improve the isolated RCY.

What is claimed is:

1. A method of producing a radiolabelled gallium complex in a form suitable for use in PET or SPECT radiopharmaceutical imaging, said method comprising reacting a $Ga^{3+}$ radioisotope in a suitable solvent with a macrocyclic bifunctional chelating agent, wherein said macrocyclic bifunctional chelating agent is linked to a targeting vector selected from the group consisting of proteins, glycoproteins, lipoproteins, polypeptides, glycopolypeptides, lipopolypeptides, peptides, glycopeptides, lipopeptides, carbohydrates, nucleic acids, oligonucleotides or small organic molecules;

characterised in that the reaction is carried out using microwave activation at 80 to 120 W for 20 s to 2 min.

2. The method according to claim 1 wherein the $Ga^{3+}$ radioisotope is selected from the group consisting of $^{66}Ga^{3+}$, $^{67}Ga^{3+}$ and $^{68}Ga^{3+}$.

3. The method according to claim 1 wherein the $Ga^{3+}$ radioisotope is $^{68}Ga^{3+}$.

4. The method according to claim 1 wherein the macrocyclic bifunctional chelating agent comprises hard donor atoms, preferably O and N atoms.

5. The method according to claim 1 wherein the target vector is a peptide or oligonucleotide.

6. The method according to claim 1 wherein the microwave activation is carried out at 90 to 110 W.

7. The method according to claim 1 wherein the microwave activation is carried out for 30 s to 90 s.

8. The method according to claim 3 wherein the $^{68}Ga^{3+}$ is obtained by contacting the eluate from a $^{68}Ge/^{68}Ga$ generator with an anion exchanger and eluting $^{68}Ga^{3+}$ from said anion exchanger.

9. The method according to claim 8 wherein the $^{68}Ge/^{68}Ga$ generator comprises a column comprising titanium dioxide.

10. The method according to claim 8 wherein the anion exchanger comprises $HCO_3^-$ as counterions.

11. The method according to claim 8 wherein the anion exchanger is an anion exchanger comprising quaternary amine functional groups, or the ion exchanger is a anion exchange resin based on polystyrene-divinylbenzene.

12. The method according to claim 1 for the production of $^{68}Ga$-radiolabelled PET tracers.

13. Method according to claim 8 wherein the eluting $^{68}Ga^{3+}$ is in the picomolar to nanomolar range after the elution, and more preferably in a nanomolar to micromolar level.

* * * * *